United States Patent [19]

Sasaki et al.

[11] 4,419,267

[45] Dec. 6, 1983

[54] PROCESS FOR REGENERATING ANTIMONY CONTAINING OXIDE CATALYST COMPRISING AN AQUEOUS AMMONIA IMPREGNATION

[75] Inventors: Yutaka Sasaki; Kunio Mori, both of Yokohama; Kiyoshi Moriya, Kanagawa; Hiroshi Utsumi, Yokohama, all of Japan

[73] Assignee: Nitto Chemical Industry Co., Ltd., Tokyo, Japan

[21] Appl. No.: 266,271

[22] Filed: May 22, 1981

[30] Foreign Application Priority Data

May 23, 1980 [JP] Japan ................................ 55-67872

[51] Int. Cl.$^3$ ..................... B01J 27/30; B01J 23/92; C07C 120/14; C07C 11/12
[52] U.S. Cl. ................................ 502/26; 260/465.3; 585/626
[58] Field of Search ............................. 252/412, 420; 260/465.3

[56]  References Cited
U.S. PATENT DOCUMENTS 2,683,122  7/1954  Woodcock et al. ................ 252/412
3,277,016 10/1966  Riesser ............................. 252/412
3,625,867 12/1971  Yoshino et al. .................... 252/456
4,165,296  8/1979  Ishii et al. ......................... 252/412
4,208,303  6/1980  Sasaki et al. ..................... 260/465.3
4,303,550 12/1981  Callahan et al. .................. 252/412
4,330,429  5/1982  Sasaki et al. ..................... 252/412

Primary Examiner—P. E. Konopka
Attorney, Agent, or Firm—Sughrue, Mion, Zinn, Macpeak and Seas

[57]  ABSTRACT

A process for regenerating an antimony containing metal oxide catalyst which comprises impregnating aqueous ammonia in an amount corresponding to the pore volume of the catalyst, to a metal oxide catalyst whose activity has been deteriorated, the catalyst containing an essential components (A) antimony, (B) at least one element selected from the group consisting of iron, cobalt, nickel, manganese, uranium, cerium, tin and copper, (C) at least one element selected from the group consisting of vanadium, molybdenum and tungsten and (D) tellurium, drying the catalyst, and calcining the catalyst in a non-reducing atmosphere at a temperature in the range of about 550° C. to about 950° C.

7 Claims, No Drawings

PROCESS FOR REGENERATING ANTIMONY CONTAINING OXIDE CATALYST COMPRISING AN AQUEOUS AMMONIA IMPREGNATION

FIELD OF THE INVENTION

This invention relates to a process for regenerating an antimony containing oxide catalyst, and more particularly to a process for regenerating an antimony containing oxide catalyst the activity of which has been deteriorated as a result of its use in oxidation, ammoxidation or oxidative dehydrogenation of hydrocarbons.

BACKGROUND OF THE INVENTION

Antimony containing metal oxide catalysts and, particularly, metal oxide compositions containing, as essential components, (A) antimony, (B) at least one element selected from the group consisting of iron, cobalt, nickel, manganese, uranium, cerium, tin and copper, (C) at least one element selected from the group consisting of vanadium, molybdenum and tungsten, and (D) tellurium, are known and are used for production of unsaturated aldehydes by oxidation of olefins, unsaturated nitriles by ammoxidation of olefins and diolefins by oxidative dehydrogenation of olefins, etc. For example, such catalysts are disclosed in U.S. Pat. No. 3,668,147, Japanese Patent Publications Nos. 19764/72, 40957/72 and 40958/72, U.S. Pat. No. 3,716,496, Japanese Patent Publications 19766/72 and 19767/72, and U.S. Pat. No. 3,988,359, etc.

In spite of their good catalytic performance, none of the above catalysts are fully satisfactory after prolonged use and their service life is not always sufficiently long. Even the activity of improved catalysts gradually decreases with extended use and improper reaction conditions often accelerate reduction in catalytic activity. It is economically unfeasible to continue using a catalyst whose activity is reduced below a certain level. In particular, when the catalyst is used industrially on the large scale as in the preparation of acrylonitrile, the influence of the deterioration is large and when the deteriorated catalyst is not replaced with fresh catalyst at the appropriate time, economical loss occurs to a remarkable extent. However, since catalysts of the above specified type are expensive, replacement of the deteriorated catalyst with fresh catalyst is a substantial expenditure. It would, therefore, be economically advantageous if a practical method for regenerating the catalyst were available.

As can be understood from the above explanation, one criterion for determining whether a catalyst is deteriorated or whether a deteriorated catalyst has been regenerated by a regeneration method is economically feasible, in contrast to a technically feasible, which takes into account the activity and selectivity of the catalyst. Based on experience a catalyst is considered "deteriorated" if the yield of the end product is reduced by more than 2 to 3% of the yield obtained using fresh catalyst, and a catalyst is considered "regenerated" if such yield is restored to the original yield level or higher.

It is difficult to enumerate the causes of catalyst deterioration which occurs during catalyst use. In most cases, many factors combine to cause such deterioration, and what is more, locating a particular contributing factor does not directly lead to the development of an effective method of regenerating the catalyst. Therefore, many attempts at providing effective catalyst regeneration have not been successful.

A method of regenerating an antimony-uranium oxide catalyst is described in U.S. patent application serial Nos. 83,187, and 103,005 (corresponding to Japanese Patent Application (OPI) No. 8615/72) (the term "OPI" as used herein refers to a "published unexamined Japanese patent application") and British Patent No. 1,365,096. That method comprises heating an antimony-uranium oxide catalyst complex in a fluidized state, in a non-reducing gas at a temperature of from 800° to 1800° F. and for a time such that the surface area of the catalyst does not fall below a minimum critical level of 5 $m^2/g$. The basic concept behind the method is to heat the catalyst before the catalyst performance, which is determined by the surface area of the catalyst, drops to a minimum critical level. In addition, the method is applicable over a wide range of temperature. Therefore, this method may be considered a satisfactorily practical method for regenerating such a catalyst. However, antimony containing oxide catalysts where antimony is combined with elements other than uranium cannot be regenerated using such a simple procedure. For example, U.S. Pat. No. 4,208,303 discloses that iron-antimony containing oxide catalysts which have a specific composition can only be regenerated under relatively limited conditions and only when the deteriorated catalyst has a specified nature. Accordingly, the method described in Japanese Patent Application (OPI) No. 8615/72 is only suitable for regenerating of an antimony-uranium oxide catalyst.

U.S. Pat. No. 4,049,575 discloses a process for the production and improvement of catalysts including a catalyst which may be regenerated in accordance with the process of this invention. In accordance with the process disclosed in U.S. Pat. No. 4,049,575 a catalyst composition is prepared by impregnating or spraying onto a mixed metal oxide composition consisting of antimony and a specific metal with a solution containing other active components. The process can be advantageously used in regenerating a deteriorated catalyst as demonstrated by the specific examples in U.S. Pat. No. 4,049,575, but the method is rather complex and costly because it involves preparing a solution of the catalytic component with which the catalyst is impregnated, impregnating the catalyst with a predetermined amount of the solution, drying, and calcining the impregnated catalyst. In particular, the method requires that the impregnating solution contain at least two catalytically active components, but it is not easy to prepare one stable impregnating solution which does not produce a precipitate, for instance. As a result, it is sometimes necessary to use rather expensive reagents as starting materials for the active components of the catalyst. The method also introduces new catalytic components to the catalyst, thus yielding a regenerated catalyst having a different composition and different physical properties than those of the original catalyst or having a different reaction rate and different optimum reaction conditions. Therefore, it is often difficult to use a catalyst regenerated in this way in combination with fresh (unregenerated) catalyst without some disadvantages occurring.

Further, Japanese Patent Application (OPI) No. 81191/79 (corresponding to U.S. patent application serial No. 959,810, field Nov. 18, 1978) provides a process for regenerating an antimony containing oxide catalyst, which comprises impregnating or spraying onto the deteriorated antimony containing oxide catalyst an aqueous solution of nitric acid and/or a nitrate and then drying the impregnated metal oxide catalyst followed by calcining the impregnated catalyst at a temperature ranging from 400° to 1000° C. The method disclosed in Japanese Patent Application (OPI) No. 81191/79 can be conducted with a wide range of catalysts to be regenerated and is a comparatively simple process from the standpoint of the regeneration operations and conditions. However, because nitric acid and/or the nitrate is very corrosive, the materials which can be used for the regenerating apparatus are extremely restricted and since large amounts of a nitric acid and nitrogen oxide are present in the waste gas, the waste gas cannot be vented to the outside, the process has the disadvantage that the apparatus for treating the waste gas must be equipped with pollution control devices to avoid pollution problems. Therefore, while the method is comparatively simple to conduct, the method has economical problems associated with its industrial use. On the other hand, in order to overcome the above problems with respect to the regeneration of the catalyst, this invention was achieved.

SUMMARY OF THE INVENTION

This invention provides the ability to eliminate the above described disadvantages in the prior processes for regenerating catalysts.

An object of this invention is to provide a process for regenerating an antimony containing metal oxide catalyst which is remarkably advantageous in industrial practice, wherein a broad range of regenerating condition can be used, the operation is simple and less difficulty with materials used for the regeneration apparatus and exhaust gas occur.

This object is achieved by a regeneration process involving calcining an antimony catalyst containing as essential components at least one element selected from the group consisting of vanadium, molybdenum and tungsten, and tellurium, which has deteriorated activity, at a temperature of 550° C.-950° C. after impregnation of a specific amount of aqueous ammonia to the deteriorated catalyst.

More specifically, this invention provides a process for regenerating an antimony containing metal oxide catalyst which comprises impregnating aqueous ammonia in an amount corresponding to the pore volume of the catalyst to a metal oxide catalyst the activity of which has been deteriorated containing as essential components (A) antimony, (B) at least one element selected from the group consisting of iron, cobalt, nickel, manganese, uranium, cerium, tin and copper, (C) at least one element selected from the group consisting of vanadium, molybdenum and tungsten, and (D) tellurium, drying the catalyst, and calcining the catalyst in a non-reducing atmosphere at a temperature in a range of about 550° C. to about 950° C.

DETAILED DESCRIPTION OF THE INVENTION

The catalyst to be regenerated in this invention is an antimony containing metal oxide catalyst by which the yield of the desired product is gradually reduced during the reaction such as oxidation, ammoxidation or oxidative dehydrogenation of hydrocarbons or is rapidly reduced because of an operational mistake (for example, incorrect determination of the feed gas composition or of the reaction temperature, etc.). The catalyst may contain, in addition to the above described essential components, one or more elements selected from the group consisting of magnesium, calcium, strontium, barium, lanthanum, titanium, zirconium, niobium, tantalum, chromium, rhenium, ruthenium, osmium, rhodium, iridium, palladium, platinum, silver, zinc, cadmium, boron, aluminum, sodium, potassium, rubidium, cesium, indium, thallium, silicon, germanium, lead, phosphorus, arsenic, bismuth, sulfur and selenium.

The composition of the antimony containing metal oxide catalyst is not restricted, but a preferred catalyst composition is represented by the following empirical formula.

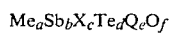

$$Me_aSb_bX_cTe_dQ_eO_f$$

In the formula, Me represents at least one element selected from the group consisting of Fe, Co, Ni, Mn, U. Ce, Sn and Cu, X represents at least one element selected from the group consisting of V, Mo and W, and Q represents at least one element selected from the group consisting of Mg, Ca, Sr, Ba, La, Ti, Zr, Nb, Ta, Cr, Re, Ru, Os, Rh, Ir, Pd, Pt, Ag, Zn, Cd, B, Al, Na, K, Rb, Cs, In, Tl, Si, Ge, Pb, P, As, Bi, S and Se. Further, a, b, c, d, e, and f each represents an atomic ratio, wherein, in case of $a=10$, then $b=5-60$ (preferably 10–50), $c=0.01-5$ (preferably 0.1–3), $d=0.02-10$ (preferably 0.1–5), $e=0-20$ (preferably 0–10) and $f=$ the number of oxygen atoms corresponding to the oxide formed by combination with the above described components.

The above described composition may or may not be supported on a carrier. Examples of suitable carriers include silica, alumina, titania, zirconia, silica alumina, etc.

The preparation of the antimony containing metal oxide catalyst to be regenerated in accordance with the process of this invention is not restricted to a specific process. For example, the process for producing the catalyst to be regenerated are disclosed in Japanese Patent Publications Nos. 19764/72, 40957/72, 40958/72, 19766/72 and 19767/72, and U.S. Pat. Nos. 3,668,147, 3,716,496 and 3,988,359. The starting materials in the preparation of the catalyst to be regenerated include Me sources such as a nitrate, an oxide, a hydroxide, a chloride, etc. of each of the elements as described above; Sb sources produced by oxidizing compounds such as antimony oxides (III, IV and V), antimony chlorides (III and V), metal antimony with a nitric acid; X sources such as an oxide and a heteropoly-acid or a salt thereof of each of the elements as described above; Te sources produced by dissolving a tellurium dioxide, tellurous acid, telluric acid, metal tellurium in nitric acid, and; Q sources such as a nitrate, an oxide, a hydroxide, a chloride, etc. of each of the elements as described above.

The aqueous ammonia used in the present invention is not particularly limited in terms of concentration. Aqueous ammonia having a concentration of about 10 to about 30% by weight commercially available on the market can be used directly or after dilution if desired. A preferred concentration is in the range of 0.5–20%. If the concentration is less than about 0.5%, the effect of regeneration is somewhat reduced. If the concentration is more than about 30%, practically use is difficult because of high volatilization of ammonia gas.

The amount of the aqueous ammonia impregnated to the deteriorated catalyst corresponds to the pore volume of the deteriorated catalyst. Measurement of the pore volume can be carried out using various known methods. The simplest method includes a water or solution absorption method for a fixed bed catalyst or a fluid catalyst and a water or solution titration method for a fluid catalyst (for a fluid bed). These methods are described in *Experimental Methods in Catalytic Research*, volume 1, edited by Robert B. Anderson, Academic Press, 1968 and *Method for Synthetic Fluid Cracking Catalysts*, American Cyanamid Company 6131-4M-1/57, the disclosure of which is incorporated herein by reference. The pore volume of the deteriorated catalyst to be regenerated in this invention is not restricted, but the pore volume of the catalyst is generally in the range of from about 0.05 to about 0.95 ml/g, and more particularly from 0.15 to 0.65 ml/g. The pore volume of the catalyst may be controlled by a variation of process of preparing a catalyst according to purposes.

The amount of the aqueous ammonia added is about 0.7 to about 1.2 times preferably 0.8 to 1.1 times the pore volume measured as described above. Utilization of the appropriate amount of aqueous ammonia is important, because regeneration becomes insufficient, if the amount of aqueous ammonia used is too small, or catalyst components, particularly, vanadium, molybdenum, tungsten and tellurium are dissolved in the aqueous ammonia and are separated or lost causing at times a deterioration of the activity, if the amount is too large. The aqueous ammonia may contain small amounts of other compounds. For example, it may contain small amounts of vanadium, molybdenum, tungsten, tellurium, boron and phosphorus, etc., compounds. However, if the amount of these compounds is large, the catalyst activity is sometimes negatively affected. Accordingly, it is preferred for these compounds to be present in an amount such that thus total amount is 10 atomic 70 or less than the amount of antimony in the catalyst. Although the concentration of ammonia easily varies because of volatilization of ammonia, there is no practical problem on use of the aqueous ammonia, because the effect of catalyst regeneration using such can be achieved over a wide concentration range as described above.

Various methods are applicable for impregnating the catalyst with aqueous ammonia. A method which comprises spraying aqueous ammonia along with stirring the deteriorated catalyst with and a method which comprises mixing the deteriorated catalyst with aqueous ammonia in a predetermined volume, in case of, particularly, a fluid catalyst, are recomended for use. It has been found that a method which comprises using an excess amount of aqueous ammonia and separating the excess by filtration is not preferred, because vanadium, molybdenum, tungsten and tellurium, etc. in the catalyst are dissolved out and lost as described above. In case of a catalyst from which the above described components have been lost, the calcinating condition of the final step in the regenerating operation must be examined. Therefore, use of an excess amount of aqueous ammonia is not practical unless there is a specific reason for using an excess.

The function of the aqueous ammonia in regenerating the catalyst in the present invention is not at present completely clear. While not desiring to be bound, it is presumed that deterioration of the antimony containing metal oxide catalyst subjected to this invention undergoes principally a reductive deterioration during the reaction. Accordingly, it is unexpected that the catalyst can be regenerated by treating with the aqueous ammonia which is a reducing material rather than a material which does not have any oxidizing property. The reason is believed to be that vanadium, molybdenum, tungsten or tellurium, as additives, contributes to a reconstruction of the catalyst, which is presumed from the knowledge that these components in the catalyst dissolve partially in aqueous ammonia. On the other hand, gaseous ammonia does not cause such a phenomenon to occur.

An aqueous solution of an amine, which is an organic base analogous to ammonia, can not be advantageously used for the purpose of this invention. It is believed that the above described phenomenon is a peculiar function of the aqueous ammonia to the catalyst of this invention.

The deteriorated catalyst impregnated with the aqueous ammonia as described above is calcined in a non-reducing atmosphere at a temperature in a range of about 550° C. to about 950° C. after drying at a temperature of less than 150° C. The calcination atmosphere should be a non-reducing atmosphere, and an oxidizing atmosphere is particularly preferred. In case of a reducing atmosphere, the catalyst components including antimony are lost by reduction with the activity deteriorating. The calcination is carried out at a temperature ranging from about 550° C. to about 950° C. for about 0.5 to about 20 hours. Where the temperature is lower than 550° C., the regeneration is less effective or ineffective. A calcination temperature of about 550° C. or higher is an essential condition, because components once dissolved in the aqueous ammonia undergo some reaction or other with the catalyst as the base. Further, where the calcination temperature is higher than about 950° C., the catalyst components, particularly, molybdenum and tellurium, etc. appear to begin to be lost, by which not only is the effect of regeneration hardly observed but also the activity and properties of the catalyst are remarkably deteriorated. Optimum calcination conditions are experimentally determined depending upon the catalyst composition and a degree of deterioration, etc. Since the temperature range is relatively wide, there is no particular problem on operation. In general, it is preferred to be near or lower than the final calcination temperature for producing the catalyst.

Since ammonia gas is generated during drying, precautions on drying must be taken when drying is carried out in the air so that an explosive mixture is not formed. If the drying is carried out using a rotary kiln under an air stream, it is possible to minimize hazards by controlling the amount of the catalyst charged. Of course, no problems arise, if the drying is carried out in the presence of an inert gas, for example, nitrogen or helium, etc. The ammonia gas generated in this case is collected in water, which can be used again for regenerating the deteriorated antimony containing metal oxide catalyst according to this invention, directly or after adjusting, as necessary, the concentration.

The apparatus for drying and calcining the catalyst is not particularly limited. A stationary furnace, a tunnel furnace, a rotory kiln and a fluidized bed calciner, etc., conventionally used for production of the catalyst, can be suitably selected and used.

The process for regenerating the deteriorated catalyst of this invention is applicable to fixed-bed catalysts and fluid catalysts. The regenerated catalyst has a restored activity, by which the yield of the desired product and the reaction rate become equal to or higher than those of fresh catalyst and the optimum reaction conditions hardly vary. Further, since the physical properties of the regenerated catalyst hardly change, the catalyst can be used in a manner similar to fresh catalyst or can be used together with fresh catalyst as a mixture. Accordingly, the industrial applications of this invention are quite advantageous.

Moreover, the process of this invention can be used as a process for previous treatment of a catalyst newly produced, by which the reaction yield and, particularly, selectivity of the desired product are sometimes improved. Although the reason for this is not presently clear, it is supposed that vanadium, molybdenum, tungsten and tellurium as the additive components contribute to catalyst reconstruction by dissolution, separating and reaction.

The present invention is illustrated in greater detail by reference to the following examples and comparative examples. However, this invention is not to be construed as being limited to these examples. Unless otherwise indicated herein, all parts, percentages, ratios and the like are by weight.

The yield and selectivity of the desired product are defined in this invention as follows:

Yield of Desired Product (%) =

$$\frac{\text{Carbon Weight of Object Product}}{\text{Carbon Weight of Hydrocarbon Fed}} \times 100$$

Selectivity of Object Product (%) =

$$\frac{\text{Yield of Object Product}}{\text{Conversion of Hydrocarbon Fed}} \times 100$$

The following conditions were used to demonstrate the activity of the catalysts in the Examples and Comparative Examples below.

Test Condition I

A fixed bed reactor having an inner diameter of 16 mm and a length of 500 mm was packed with 30 ml of catalyst and heated in a molten salt bath comprising a mixture of equal weights of sodium nitrite and potassium nitrate. The reactor was fed with a gas of the following composition at a rate of 7.5 l (NTP) per hour. The reaction pressure was atmospheric.
Air/1-Butene=5 (molar ratio)
Water/1-Butene=1.5 (molar ratio)

Test Condition II

A fixed bed reactor having an inner diameter of 16 mm and a length of 500 mm was packed with 25 ml of catalyst and heated in a molten salt bath comprising a mixture of equal weights of sodium nitrite and potassium nitrate. The reactor was fed with a gas of the following composition at 12 liters (NTP) per hour. The reaction pressure was atmospheric.
Air/Isobutene=16.7 (molar ratio)
Ammonia/Isobutene=1.3 (molar ratio)
Water/Isobutene=4.0 (molar ratio)

Test Condition III

A fixed bed reactor having an inner diameter of 16 mm and a length of 500 mm was packed with 30 ml of catalyst and heated in a molten salt bath comprising a mixture of equal weights of sodium nitrite and potassium nitrate. The reactor was fed with a gas of the following composition at 10 liters (NTP) per hour. The reaction pressure was atmospheric.
Air/Propylene=10.5 (molar ratio)
Ammonia/Propylene=1.05 (molar ratio)

Test Condition IV

A fluidized bed reactor having an inner diameter of 2 inches at the reaction zone and a height of 2 m was packed with catalyst. The reactor was fed with a starting gas (propylene, ammonia and water) of the following composition at an apparent linear velocity of 15 cm/sec.
Air/Propylene=10.5 (molar ratio)
Ammonia/Propylene=1.05 (molar ratio)
The contact time is defined as follows:

$$\text{Contact Time (sec)} = \frac{\text{Volume of Packed Catalyst (based on apparent bulk density) (l)}}{\text{Velocity of Feed Gas under Temperature and Pressure Used as Reaction Conditions (l/sec)}}$$

The reaction pressure was atmospheric.

EXAMPLE 1

A catalyst having the empirical formula of $Fe_{10}Sb_{25}W_{0.25}Te_{1.0}O_{67.8}(SiO_2)_{30}$ was prepared as follows.

60.9 g of metallic antimony powder was added portionwise to 225 ml of nitric acid (specific gravity: 1.38) heated to 80° C. After the termination of the generation of a brown gas following the completion of the addition of the antimony, the mixture was allowed to stand at room temperature (about 20°–30° C.) for 16 hours. Thereafter, excess nitric acid was removed and the precipitate was washed 3 times with 100 ml portions of water. Product (I)

11.2 g of electrolytic iron powder was added portionwise to a solution of 81 ml of nitric acid (specific gravity: 1.38) and 100 ml of water and dissolved therein completely. Product (II)

1.3 g of ammonium paratungstate was dissolved in 50 ml of water. 4.6 g of telluric acid was added to the solution of ammonium paratungstate prepared above and dissolved. Product (III)

As the carrier component, 180 g of silica sol (20% by weight of $SiO_2$) was weighed out. Product (IV)

(II) and (IV) were mixed together and (III) was added thereto to obtain a liquid mixture which was then mixed with (I), to which aqueous ammonia (28%) was gradually added with stirring to adjust the pH to 2. This mixture was then heated with stirring and evaporated to dryness.

The dried product was crushed and calcined at 200° C. for 2 hours and then at 400° C. for 2 hours, after which water was added. The mixture was mixed together and was molded into tablets of a size of 2 mm×2 mm ϕ. The tablets were dried at 130° C. for 16 hours and then calcined at 850° C. for 3 hours.

When the activity of this catalyst was tested by reacting at a reaction temperature of 370° C. according to the Test Condition I described above, the conversion of butene-1 was 93% and the yield of butadiene was 83%. The amount of air fed was temporarily reduced and then restored to the prescribed condition. The conversion of butene-1 became 88% and the yield of butadiene became 77%.

This catalyst was discharged from the reactor and regenerated according to the process of this invention. Namely, with stirring this deteriorated catalyst (pore volume: 0.38 ml/g), was sprayed with about 15 ml of a 10% aqueous ammonia to impregnate the catalyst sufficiently. By this treatment, about 15 ml of aqueous ammonia was absorbed. Thereafter, the temperature was gradually increased. After drying at 120° C. for 16 hours, the catalyst was calcined at 800° C. for 5 hours in the air. When this regenerated catalyst was used for reaction according to the same Test Condition I as described above, the conversion of butene-1 was 95% and the yield of butadiene was 85%.

EXAMPLE 2

A catalyst having the empirical formula of $U_{10}Sb_{50}W_{0.25}Te_{1.0}O_{129.4}(SiO_2)_{60}$ was prepared as follows.

60.9 g of metallic antimony powder (less than 100 mesh) was added portion-wise to 22.5 ml of nitric acid (specific gravity: 1.38) heated to 80° C. After the termination of the generation of a brown gas following the completion of the addition of antimony, the mixture was allowed to stand at a room temperature for 16 hours. Thereafter, excess nitric acid was removed and the precipitate was washed 3 times with 100 ml portions of water. Product (I).

50.2 g of uranyl nitrate $UO_2(NO_3)_2.6H_2O$ was dissolved in 100 ml of water. Product (II)

0.65 g of ammonium tungstate $5(NH_4)_2O.12WO_3.5H_2O$ was dissolved in 50 ml of water. Product (III)

As the carrier component, 180.3 g of silica sol (20% by weight of $SiO_2$) was weighed out. Product (IV)

(II) and (IV) were mixed together and (III) was added thereto to produce a liquid mixture which was then mixed with (I). This mixture was heated while stirring the mixture well and evaporated to dryness. The dried product was crushed and calcined at 200° C. for 2 hours and then at 400° C. for 2 hours. Then water was added thereto for mixing and the mixture was molded into tablets of a size of 2 mm × 2 mm $\phi$. After drying at 130° C. for 16 hours, the tablets were calcined at 830° C. for 3 hours.

When the activity of this catalyst was tested by reaction at 400° C. according to Test Condition I describe above, the conversion of butene-1 was 95% and the yield of butadiene was 79%. The amount of air fed was temporarily reduced and it was then restored to the prescribed condition. The conversion of butene-1 was reduced to 82% and the yield of butadiene was reduced to 73%.

This deteriorated catalyst was discharged from the reactor and regenerated according to the process of this invention. Namely, about 10 ml of a 10% aqueous ammonia was sprayed onto this deteriorated catalyst (pore volume: 0.32 ml/g) with stirring to impregnate the catalyst sufficiently. The catalyst was kept at 50° C. for 16 hours in a closed system. After the temperature was gradually increased to dry the catalyst at 120° C. for 16 hours, the catalyst was calcined at 800° C. for 2 hours. When the regenerated catalyst was evaluated according to Test Condition I, the conversion of butene-1 was 95% and the yield of butadiene was 80%.

EXAMPLE 3

A catalyst having the empirical formula of $S_{10}Sb_{25}V_{0.25}Te_{1.0}O_{72.6}(SiO_2)_{30}$ was prepared as follows.

60.0 g of metallic antimony powder (less than 100 mesh) and 23.7 g of metallic tin powder (less than 100 mesh) were added portion-wise to 500 ml of nitric acid (specific gravity: 1.38) heated to 80° C. After the termination of the generation of a brown gas, the mixture was allowed to stand at room temperature for 16 hours. Thereafter, excess nitric acid was removed and the precipitate was washed 3 times with 100 ml portions of water. Product (I)

0.58 g of ammonium metavanadate, $NH_4NO_3$, was dissolved in 150 ml of water. 4.55 g of telluric acid, $H_6TeO_6$, was weighed out and dissolved in the prepared solution of ammonium metavanadate. Product (II)

As the carrier component, 180.3 g of silica sol (20% by weight of $SiO_2$) was weighed out. Product (III)

A solution prepared by mixing (II) with (III) was mixed with (I), and the mixture was heated while stirring the mixture well to evaporate to dryness. The dried product was crushed and calcined at 200° C. for 2 hours and then at 400° C. for 2 hours. Thereafter water was added thereto and kneaded together. The mixture was then molded into pellets. After drying at 130° C. for 16 hours, the pellets were calcined at 900° C. for 2 hours.

The activity of this catalyst was tested by reaction at 430° C. according to Test Condition II described above. In the initial period of the reaction, the conversion of isobutene was 96% and the yield of methacrylonitrile was 68%. After the test was carried out by varying the reaction temperature and reducing the molar ratio of ammonia/isobutene fed, the conditions were restored to the initial reacting conditions, by which the conversion of isobutene and the yield of methacrylonitrile decreased to 92% and 60%, respectively.

This deteriorated catalyst was discharged from the reactor and regenerated according to the process of this invention. Namely, about 11 ml of 28% aqueous ammonia was sprayed onto this deteriorated catalyst (pore volume: 0.42 ml/g) to impregnate the catalyst sufficiently. After it was dried at 120° C. for 16 hours, the catalyst was calcined at 850° C. for 3 hours in air. When the activity of the resulting catalyst was tested under the same conditions as those for the catalyst prior to deterioration, the conversion of isobutene was 95% and the yield of methacrylonitrile was 68%.

EXAMPLE 4

A catalyst having the empirical formula of $Fe_{10}Sb_{1.5}Mo_{1.5}Te_5Cu_{1.0}P_{0.5}O_{60.6}(SiO_2)_{60}$ was prepared as follows.

28.0 g of electrolytic iron powder and then 32.0 g of metallic tellurium were added portion-wise to a solution of 400 ml of nitric acid (specific gravity: 1.38) and 530 ml of water and completely dissolved therein. To the resulting solution, 12.1 g of copper nitrate $Cu(NO_3)_2.3H_2O$ and then 2.9 g of phosphoric acid (85%) were added. Product (I)

13.3 g of ammonium paramolybdate, $(NH_4)_6Mo_7O_{24}.4H_2O$, was dissolved in 904 g of silica sol (20% by weight of $SiO_2$) with heating. Product (II)

To a solution prepared by mixing (I) with (II), 109.7 g of antimony trioxide powder was added. After the pH was adjusted to 3 with 15% aqueous ammonia, the resulting liquid suspension was refluxed by heating to 100° C. with stirring, followed by evaporation to dryness. The dried product was calcined at 200° C. for 2 hours and 400° C. for 2 hours. Thereafter, water was added thereto and kneaded together. The mixture was then molded into cylindrical pellets of a size of 2 mm × 2 mm $\phi$. The pellets were then calcined at 200° C. for 2 hours, at 400° C. for 2 hours and finally at 700° C. for 4 hours.

The activity of this catalyst was carried out by reaction at 440° C. according to Test Condition III described above. The conversion of propylene was 99% and the yield of acrylonitrile was 81%. Then, the molar ratio of air/propylene fed was reduced, by which the activity deteriorated. The conditions were restored to the initial conditions and the activity was evaluated. The conversion of propylene and the yield of acrylonitrile decreased to 95% and 75%, respectively.

This deteriorated catalyst was discharged from the reactor and regenerated according to the process of this invention. This deteriorated catalyst was sufficiently impregnated with 5% aqueous ammonia containing 0.35% of ammonium paramolybdate in an amount corresponding to the pore volume (0.29 ml/g) and the catalyst was then allowed to stand at room temperature for about 5 hours. After the catalyst was dried at 120° C. for 16 hours, the catalyst was calcined at 680° C. for 5 hours. When the activity of the resulting catalyst was tested under the same condition as that for the catalyst prior to deterioration, the conversion of propylene was 97% and the yield of acrylonitrile was 81%. The amount of the Mo component added in the regeneration step was 0.3 to 100 of Sb on an atomic ratio basis.

EXAMPLE 5

A catalyst having the empirical formula of $Cr_2W_{0.5}Te_{1.0}Fe_{10}Sb_{25}O_{71.5}(SiO_2)_{30}$ was prepared as follows.

2.91 kg of antimony trioxide powder (less than 20μ) was weighed out. Product (I)

447 of electrolytic iron powder was weighed. 3.2 l of nitric acid (specific gravity: 1.38) was mixed with water with heating. To this solution, the iron powder was added portion-wise and completely dissolved therein. 102 g of tellurium powder was then added portionwise to the resulting solution and completely dissolved therein. Product (II)

104 g of ammonium paratungstate was dissolved in 5 liters of water with heating. Product (III)

320 g of chromium nitrate $Cr(NO_3)_3.9H_2O$ was dissolved in 1.5 liters of water. Product (IV)

7.21 kg of silica sol (20% by weight of $SiO_2$) was weighed out. Product (V)

(I)–(V) were mixed together, and aqueous ammonia was added portion-wise thereto with stirring to adjust the pH to 2. The mixture was heated at 100° C. for 3 hours with stirring.

The resulting slurry was dried by conventional spray drying using a spray drier. The resulting microspheroidal particles were calcined at 250° C. for 2 hours, and then at 450° C. for 2 hours, and they were finally calcined at 810° C. for 5 hours.

The activity of this catalyst was tested reaction at 460° C. according to Test Condition IV. The conversion of propylene was 98.4% and the yield of acrylonitrile was 77.7%. When the reaction was continued as it was, the flow amount of ammonia reduced and generation of carbon dioxide increased. The oxygen concentration in the outlet part became zero which meant a deterioration of the catalyst. When the condition was restored to the initial prescribed condition, the conversion of propylene and the yield of acrylonitrile described to 95.1% and 73.0%, respectively.

This deteriorated catalyst was discharged from the reactor and regenerated according to the process of this invention. 15% aqueous ammonia was added in an amount corresponding to the pore volume (0.44 ml/g) to this deteriorated catalyst, and the mixture was blended for 1 hour. Thus the pores of the catalyst were sufficiently filled with the aqueous ammonia. After drying at 120° C. for 16 hours, the catalyst was calcined at 800° C. for 2 hours. When the activity of this catalyst was tested under the same condition as that of the catalyst prior to deterioration, the conversion of propylene was 99.3% and the yield of acrylonitrile was 78.0%.

EXAMPLE 6

A catalyst having the empirical formula of $Mg_2Mo_{0.25}Te_{1.0}Co_{1.0}Fe_{10}Sb_{25}O_{70.8}(SiO_2)_{60}$ was prepared by the same process as in Example 5.

However, magnesium nitrate was used instead of chromium nitrate and ammonium paramolybdate was used instead of ammonium paratungstate. Final calcination of the catalyst was carried out at 820° C. for 5 hours.

The activity of this catalyst was tested by reaction at 460° C. according to Test Condition IV. The conversion of propylene was 98.5% and the yield of acrylonitrile was 77.3%. Subsequently, the reaction was carried out under various conditions by changing the reaction conditions. However, since the reaction was carried out by keeping the lower molar ratio of fed air/propylene for a long period of time, the yield of acrylonitrile under the initial condition became 74.1%.

This deteriorated catalyst was discharged from the reactor and regenerated according to the process of this invention. 5% aqueous ammonia was added in an amount corresponding to the pore volume (0.38 ml/g) to this deteriorated catalyst, and the mixture was blended for 1 hour, by which the fine openings of the catalyst were sufficiently filled. After drying at 120° C. for 16 hours, it was calcined at 800° C. for 2 hours. When the activity of this catalyst was tested under the same condition as that of the catalyst prior to deterioration the conversion of propylene was 98.0% and the yield of acrylonitrile was 77.4%.

EXAMPLE 7

A catalyst having the empirical formula of $Ce_2W_{0.5}Te_{1.0}Fe_{10}Sb_{25}O_{72.5}(SiO_2)_{30}$ was prepared by the same process as in Example 1. However, cerium nitrate was used as a Ce source. The final calcination was carried out at 850° C. for 3 hours.

When this catalyst was used for reaction at 460° C. according to Test Condition III, the conversion of propylene was 99% and the yield of acrylonitrile was 77.5%. When the reaction was carried out and the amount of air fed was reduced to decrease the oxygen concentration in the outlet gas to nearly zero, the amount of carbon dioxide had a tendency to increase. Thus, the condition was restored to the prescribed condition. The conversion of propylene decreased to 90% and the yield decreased to 73%.

This catalyst was discharged from the reactor and regenerated according to the process of this invention. Namely, 5% aqueous ammonia containing 0.86% of telluric acid was sprayed in an amount corresponding to the pore volume (0.47 ml/g) onto this deteriorated catalyst, and the catalyst sufficiently impregnated. Then the temperature was gradually increased. After drying at 120° C. for 16 hours, the catalyst was calcined at 790° C.

or 5 hours. When the activity of resulting regenerated catalyst was tested under the same condition as that for the catalyst prior to deterioration, the conversion of propylene was 99% and the yield of acrylonitrile was 78%. The amount of Te component added in the regeneration step was 0.5 to 100 of Sb on an atomic ratio basis.

EXAMPLE 8

A catalyst having the empirical formula of $Fe_{10}Sb_{2.5}Mo_{0.3}Te_{1.0}Bi_2O_{68.7}(SiO_2)_{30}$ was prepared by the same process as in Example 1. However, ammonium paramolybdate was used as the Mo source and bismuth nitrate was used as the Bi source. The final calcination of the catalyst was carried out at 790° C. for 5 hours.

When this catalyst was reacted at 430° C. according to Test Condition III, the conversion of propylene was and the yield of acrylonitrile was 77%. When the reaction was carried out and the amount of air fed reduced to decrease the oxygen concentration in the outlet gas to nearly zero, the amount of carbon dioxide had a tendency to increase. Thus the condition was restored to the prescribed condition. The conversion of propylene decreased to 95% and the yield of acrylonitrile decreased to 73%.

This catalyst was discharged from the reactor and regenerated according to the process of this invention. Namely, 25% aqueous ammonia was added in an amount of 1.1 times of the pore volume (0.45 ml/g) to this deteriorated catalyst with stirring to permeate the catalyst. After the catalyst was dried at 120° C. for 16 hours, the catalyst was calcined at 780° C. for 5 hours. When the resulting regenerated catalyst was evaluated under the same condition as that for the catalyst prior to deterioration, the conversion of propylene was 98% and the yield of acrylonitrile was 77.5%.

EXAMPLE 9

A catalyst having the empirical formula of $Fe_{10}Sb_{2.5}Mo_{0.3}Te_{1.0}Mn_1B_1O_{71.4}(SiO_2)_{30}$ was prepared by the same process as in Example 1. However, ammonium paramolybdate was used as the Mo source, manganese nitrate was used as the Mn source and boric acid was used as the B source. The final calcination of the catalyst was carried out at 800° C. for 5 hours.

When this catalyst was reacted at 430° C. according to Test Condition III, the conversion of propylene was 98% and the yield of acrylonitrile was 78. When the reaction was continued, while gradually reducing the amount of ammonia fed, formation of acrolein and carbon dioxide became marked and there was fear of deteriorating the catalyst. The condition was restored to the initial test condition, but the conversion of propylene was 97% and the yield of acrylonitrile was 76%, which meant evident deterioration.

This deteriorated catalyst was discharged from the reactor and regenerated according to the process of this invention. Namely, 28% aqueous ammonia was added in an amount of 0.9 times of the pore volume (0.38 ml/g) to the catalyst, and the mixture was well blended to permeate the catalyst with the aqueous ammonia. After drying at 120° C. for 16 hours, the catalyst was calcined at 790° C. for 1 hour. When the activity of this regenerated catalyst was tested under the same condition as the case of the catalyst prior to deterioration, the conversion of propylene was 97% and the yield of acrylonitrile was 78%.

EXAMPLE 10

A catalyst having the empirical formula of $Al_2W_{0.5}Te_{1.0}Fe_{10}Sb_{25}O_{71.5}(SiO_2)_{30}$ was prepared by the same process as in Example 1. However, aluminium nitrate was used as the Al source. The final calcination of the catalyst was carried out at 850° C. for 5 hours.

When this catalyst was reacted at 450° C. according to Test Condition III, the conversion of propylene was 99% and the yield of acrylonitrile was 76%. When the reaction was carried out while reducing the amount of air fed to decrease the oxygen concentration in the outlet gas to nearly zero, carbon dioxide had a tendency to increase. Thus the condition was restored to the prescribed condition. The conversion of propylene decreased to 96% and the yield of acrylonitrile decreased to 73%.

This catalyst was discharged from the reactor and regenerated according to the process of this invention. Namely, about 11 ml of 5% aqueous ammonia was sprayed onto this deteriorated catalyst (pore volume: 0.4 ml/g) with stirring to sufficiently impregnate the catalyst with aqueous ammonia. After drying at 120° C. for 16 hours, the catalyst was calcined at 800° C. for 4 hours. When this regenerated catalyst was evaluated under the same condition as that for the catalyst prior to deterioration, the conversion of propylene was 98% and the yield of acrylonitrile was 77%.

EXAMPLE 11

A catalyst having the empirical formula of $U_{10}Sb_{2.0}Ti_{0.5}Zr_{0.5}Mo_{0.2}Te_{1.0}O_{71.3}(SiO_2)_{60}$ was prepared by the same process as in Example 2. However, titanium dioxide was used as the Ti source and zirconium oxynitrate was used as the Zr source. The final calcination of the catalyst was carried out at 860° C. for 5 hours.

When the activity of this catalyst was tested according to Test Condition III, the conversion of propylene was 99% and the yield of acrylonitrile was 81%. When the reaction was carried out while reducing the amount of air fed to decrease the oxygen content in the outlet gas to nearly zero, the amount of carbon dioxide rapidly increased, which meant deterioration of the catalyst. When the reaction was carried out by restoring the prescribed condition, the conversion of propylene and the yield of acrylonitrile greatly decreased to 88% and 69%, respectively.

This catalyst was discharged from the reactor and regenerated according to the process of this invention. Namely, about 14 ml of 28% aqueous ammonia was sprayed onto this deteriorated catalyst (pore volume: 0.35 ml/g) with stirring, to sufficiently impregnate the catalyst with aqueous ammonia. After drying at 120° C. for 16 hours, the catalyst was calcined at 840° C. for 5 hours. When this regenerated catalyst was examined under the same condition as that for the catalyst prior to deterioration, the conversion of propylene was 97% and the yield of acrylonitrile was 79%.

EXAMPLE 12

A catalyst having the empirical formula of $Fe_{10}Sb_{20}V_{0.1}Mo_{0.1}W_{0.6}Te_{1.5}Zn_2O_{62.4}(SiO_2)_{80}$ was prepared by the same process as in Example 5. However, the amount of production was 10 times the amount in Example 5, ammonium metavanadate was used as the V source, ammonium paramolybdate was used as the Mo source and zinc nitrate was used as the Zn source. The final calcination of the catalyst was carried out at 760° C. for 4 hours.

A fluidized bed reactor having an inner diameter of 8 inches at the catalyst flowing zone was packed with this catalyst, and an ammoxidation of propylene was carried out.

Test Condition

Reaction Pressure: 0.5 kg/cm$^2$G
Molar ratio of Feed Gas:
 Oxygen (fed as air)/Propylene=2.2 (molar ratio)
 Ammonia/Propylene=1.1 (molar ratio)

Under this condition, the evaluation was carried out at a reaction temperature of 440° C. for 300 hours. Although good reaction results were obtained, difficulty occurred with the compressor just before conclusion of the evaluation, by which the oxygen concentration of the reaction gas became zero. Since the reaction was continued under such a condition for about 1.5 hours, the yield of acrylonitrile was reduced about 3% as compared with that at initiation of the reaction.

This deteriorated catalyst was discharged and 4 kg thereof was weighed out. 1.3 liters of 10% aqueous ammonia were mixed with this deteriorated catalyst (pore volume: 0.34 ml/g). After mixing for 1 hour to permeate the aqueous ammonia into the catalyst well, the catalyst was dried at 120° C. for 5 hours. 2 kg of the catalyst was weighed out and calcined at 720° C. for 5 hours. The balance was calcined at 740° C. for 5 hours.

The activity of catalysts before and after deterioration and catalysts regenerated by the process of this invention were tested according to Test Condition IV. The results obtained are shown in Table 2 below.

Comparative Example 1

2 kg of the deteriorated catalyst formed in Example 12 was weighed out and mixed with 3 liters of 10% aqueous ammonia with stirring for 1 hour. After the excess aqueous ammonia was removed by centrifugal separation, the catalyst was dried at 120° C. for 5 hours, and thereafter calcined at 740° C. for 5 hours. The activity of this catalyst was tested according to Test Condition IV. The results are shown in Table 2 below.

Comparative Example 2-a 2 kg of the deteriorated catalyst formed in Example 12 was weighed out, and was charged in an externally heated fluidized bed calciner having an inner diameter of 4 inches and calcined at 720° C. for 5 hours.

Comparative Example 2-b 2 kg of the deteriorated catalyst formed in Example 12 was weighed out and calcined by the same process as in Comparative Example 2-a except that the calcination temperature was 740° C. and the time, was 5 hours.

These catalysts in Comparative Examples 2-a and 2-b were evaluated according to Test Condition IV described above. The results are shown in Table 2 below.

The results of the activity in Examples 1–4 and 7–11 are collectively described in Table 1 below and results of the activity in Examples 5, 6 and 12 and Comparative Examples 1 and 2 are collectively described in Table 2 below.

EXAMPLE 13

A catalyst having the empirical formula of $Fe_{12}Sb_{25}V_{0.1}Mo_{0.3}W_{0.3}Te_{1.5}Cu_3O_{76.05}(SiO_2)_{60}$ was prepared by the same process as in Example 5. However, the amount of production was 10 times the amount in Example 5, ammonium metavanadate was used as the V source, ammonium paramolybdate was used as the Mo source and copper nitrate $Cu(NO_3)_2.6H_2O$ was used as the Cu source. The final calcination calcination of the catalyst was carried out at 790° C. for 5 hours.

A fluidized bed reactor having an inner diameter of 8 inches at the catalyst flowing zone was packed with this catalyst, and ammoxidation of propylene was carried out.

Test Condition

Reaction Pressure: 0.5 kg/cm$^2$G
Molar Ratio of Feed Gas:
 $O_2$(fed as air)/Propylene=2.0 (molar ratio)
 $NH_3$/Propylene=1.00 (molar ratio)

Under this condition, the reaction was carried out at a reaction temperature of 450° C. During the reaction, the molar ratio of oxygen/propylene was gradually reduced and the reaction temperature was increased 10°–20° C., by which the oxygen concentration in the exit gas became nearly zero. The reaction was carried out in this state for 3 hours. Thereafter, the condition was restored to the initial reaction condition. The yield of acrylonitrile was reduced and formation of carbon dioxide gas became marked.

This deteriorated catalyst was discharged and 4 kg was weighed out. Since the pore volume was 0.30 ml/g, 1.2 liters of 15% aqueous ammonia were weighed out and mixed with the deteriorated catalyst. After mixing for 1 hour, the catalyst was dried at 120° C. for 16 hours and calcined at 750° C. for 2 hours.

Comparative Example 3-a 2 kg of the deteriorated catalyst formed in Example 13 was weighed out and was charged in an externally heated fluidized bed furnace having an inner diameter of 4 inches and calcined at 730° C. for 5 hours.

Comparative Example 3-b 2 kg of the deteriorated catalyst formed in Example 13 was weighed out and calcined by the same process as in Comparative Example 3-a. However, the calcination temperature was 750° C. and the time was 5 hours.

These catalysts in Example 13 and Comparative Examples 3-a and 3-b were evaluated according to Test Condition IV described above. The results are shown in Table 2 below.

TABLE 1

| | Test Condition | Object Product | Reacting Condition - Result of Reaction | | | |
|---|---|---|---|---|---|---|
| | | | Reaction Temperature (°C.) | Yield of Object Product (%) | Conversion of Hydrocarbon Fed (%) | Selectivity of Object Product (%) |
| Example 1 | | | | | | |
| Before deterioration | I | Butadiene | 370 | 83 | 93 | 89 |
| After deterioration | " | " | " | 77 | 88 | 87.5 |
| Regeneration | " | " | " | 85 | 95 | 89.5 |

TABLE 1-continued

| | Test Condition | Object Product | Reaction Temperature (°C.) | Yield of Object Product (%) | Conversion of Hydrocarbon Fed (%) | Selectivity of Object Product (%) |
|---|---|---|---|---|---|---|
| Example 2 | | | | | | |
| Before deterioration | I | Butadiene | 400 | 79 | 95 | 83 |
| After deterioration | " | " | " | 73 | 91 | 80 |
| Regeneration | " | " | " | 80 | 95 | 84 |
| Example 3 | | | | | | |
| Before deterioration | II | Methacrylonitrile | 430 | 68 | 96 | 71 |
| After deterioration | " | " | " | 60 | 92 | 65 |
| Regeneration | " | " | " | 68 | 95 | 72 |
| Example 4 | | | | | | |
| Before deterioration | III | Acrylonitrile | 440 | 81 | 99 | 82 |
| After deterioration | " | " | " | 75 | 95 | 79 |
| Regeneration | " | " | " | 81 | 97 | 83.5 |
| Example 7 | | | | | | |
| Before deterioration | III | Acrylonitrile | 460 | 77.5 | 99 | 78 |
| After deterioration | " | " | " | 73 | 90 | 81 |
| Regeneration | " | " | " | 78 | 99 | 79 |
| Example 8 | | | | | | |
| Before deterioration | III | Acrylonitrile | 430 | 77 | 98 | 79 |
| After deterioration | " | " | " | 73 | 95 | 77 |
| Regeneration | " | " | " | 77.5 | 98 | 79 |
| Example 9 | | | | | | |
| Before deterioration | III | Acrylonitrile | 430 | 78 | 98 | 79.5 |
| After deterioration | " | " | " | 76 | 97 | 78 |
| Regeneration | " | " | " | 78 | 97 | 80 |
| Example 10 | | | | | | |
| Before deterioration | III | Acrylonitrile | 450 | 76 | 99 | 77 |
| After deterioration | " | " | " | 73 | 96 | 76 |
| Regeneration | " | " | " | 77 | 98 | 78.5 |
| Example 11 | | | | | | |
| Before deterioration | III | Acrylonitrile | 470 | 81 | 99 | 82 |
| After deterioration | " | " | " | 69 | 88 | 78 |
| Regeneration | " | " | " | 79 | 97 | 81 |

TABLE 2

| | Final Calcination Condition at Regeneration | Test Condition | Reacting Condition Reacting Temperature | Contact Time | Yield of Acrylonitrile | Conversion of Propylene | Selectivity of Acrylonitrile |
|---|---|---|---|---|---|---|---|
| Example 5 | | | | | | | |
| Before deterioration | (810° C., 5 hrs) | IV | 460° C. | 4.5 sec. | 77.7% | 98.4% | 79.0% |
| After deterioration | " | " | " | " | 73.0 | 95.1 | 76.8 |
| Regeneration | 800° C., 2 hrs | " | " | " | 78.0 | 99.3 | 78.5 |
| Example 6 | | | | | | | |
| Before deterioration | (820° C., 5 hrs) | " | 460 | 5.5 | 77.3 | 98.5 | 78.5 |
| After deterioration | " | " | " | " | 74.1 | 93.5 | 79.3 |
| Regeneration | 800° C., 2 hrs | " | " | " | 77.4 | 98.0 | 79.0 |
| Example 12 | | | | | | | |
| Before deterioration | (760° C., 4 hrs) | " | 450 | 3.5 | 81.5 | 99.2 | 82.2 |
| After deterioration | " | " | " | " | 78.3 | 97.1 | 80.6 |
| Regeneration | 720° C., 5 hrs | " | " | " | 81.8 | 99.5 | 82.2 |
| Regeneration | 740° C., 5 hrs | " | " | " | 82.1 | 99.0 | 82.9 |
| Comparative Example 1 | 740° C., 5 hrs | " | " | " | 62.4 | 88.9 | 70.2 |
| Comparative Example 2-a | 720° C., 5 hrs | " | " | " | 79.8 | 98.4 | 81.1 |
| Comparative Example 2-b | 740° C., 5 hrs | " | " | " | 81.0 | 98.9 | 81.9 |
| Example 13 | | | | | | | |
| Before deterioration | (790° C., 5 hrs) | " | " | 3.0 | 82.8 | 98.9 | 83.7 |
| After deterioration | " | " | " | " | 71.2 | 91.0 | 78.2 |
| Regeneration | (750° C., 2 hrs) | " | " | " | 82.5 | 98.2 | 84.0 |
| Comparative Example 3-a | 730° C., 5 hrs | " | " | " | 77.6 | 95.3 | 81.4 |
| Comparative Example 3-b | 750° C., 5 hrs | " | " | " | 77.8 | 95.0 | 81.9 |

Note:
( ) denotes final calcination condition at preparation of the catalyst.

It is obvious from the results of Examples 1 to 12 that the process of this invention is useful for regeneration of these kinds of catalysts. In each case, the activity of the catalyst has been restored so that the catalyst has an activity equal to or higher than that of fresh catalyst.

On the contrary, where the deteriorated catalyst is regenerated using a large amount of aqueous ammonia without applying the process of this invention, the activity is deteriorated as shown in Comparative Example 1. This reason is believed to be useful catalyst components, particularly, V, Mo, W and Te, etc., are dissolved out by the aqueous ammonia.

In Comparative Examples 2-a and 2-b wherein the regeneration is carried out by the process described in U.S. Pat. No. 4,208,303, the catalyst can be regenerated relatively well. However, the process of this invention in Example 12 provides higher efficiency on the whole. Further, the process described in U.S. Pat. 4,208,303 can be applied only to regeneration of specific iron-antimony catalysts. On the contrary, the process of this invention is quite advantageous in that it can be applied to other antimony containing catalysts.

In Example 13, the degree of deterioration is greater than that in Example 12. In Comparative Examples 3a and 3b, the regeneration is carried out by the process described in U.S. Pat. No. 4,208,303 similar to the cases of Comparative Examples 2-a and 2-b. Recovery of activity is quite inferior to that in Comparative Examples 2-a and 2-b. On the other hand, in Example 13 according to the process of this invention, recovery of the activity is satisfactory. Namely, it can be seen that the process of this invention can be used for regeneration of the activity catalyst of where the activity has been remarkably deteriorated.

While the invention has been described in detail and with reference to specific embodiments thereof, it will be apparent to one skilled in the art that various changes and modifications can be made therein without departing from the spirit and scope thereof.

What is claimed is:

1. A process for regenerating an antimony containing metal oxide catalyst which comprises impregnating aqueous ammonia in an amount corresponding to the pore volume of the catalyst, into a metal oxide catalyst whose activity has been deteriorated, said catalyst containing as essential components (A) antimony, (B) at least one element selected from the group consisting of iron, cobalt, nickel, manganese, uranium, cerium, tin and copper, (C) at least one element selected from the group consisting of vanadium, molybdenum and tungsten and (D) tellurium, drying the catalyst, and calcining the catalyst in a non-reducing atmosphere at a temperature in the range of about 550° C. to about 950° C.

2. The process according to claim 1, wherein the antimony containing metal oxide catalyst is a metal oxide catalyst containing, in addition to said components (A) to (D), (E) at least one element selected from the group consisting of magnesium, calcium, strontium, barium, lanthanum, titanium, zirconium, niobium, tantalum, chromium, rhenium, ruthenium, osmium, rhodium, iridium, palladium, platinum, silver, zinc, cadmium, boron, aluminum, sodium, potassium, rubidium, cesium, indium, thallium, silicon, germanium, lead, phosphorus, arsenic, bismuth, sulfur and selenium.

3. The process according to claim 2, wherein the antimony containing metal oxide catalyst is a metal oxide catalyst having the empirical formula $$Me_aSb_bX_cTe_dQ_eO_f$$

where Me represents at least one element selected from the group consisting of Fe, Co, Ni, Mn, U, Ce, Sn and Cu, X represents at least one element selected from the group consisting of V, Mo and W, and Q represents at least one element selected from the group consisting of Mg, Ca, Sr, Ba, La, Ti, Zr, Nb, Ta, Cr, Re, Ru, Os, Rh, Ir, Pd, Pt, Ag, Zn, Cd, B, Al, Na, K, Rb, Cs, In, Tl, Si, Ge, Pb, P, As, Bi, S and Se; and a, b, c, d, e and f represent each atomic ratios, wherein, when a=10, b=5–60, c=0.01–5, d=0.02–10, e=0–20 and f=the number of oxygen atoms corresponding to the oxide thereof.

4. The process according to claim 1, 2 or 3, wherein the concentration of aqueous ammonia used is about 0.5 to 30% by weight.

5. The process according to claim 1, 2 or 3, wherein the amount of aqueous ammonia used is about 0.7 to about 1.2 times the pore volume of the catalyst to be impregnated.

6. The process according to claim 1, 2 or 3, wherein the pore volume of the catalyst is 0.05 to 0.95 ml/g.

7. The process according to claim 1, 2 or 3, wherein the pore volume of the catalyst is 0.15 to 0.65 ml/g.

* * * * *